United States Patent [19]
D'Agaro

[11] Patent Number: 5,514,344
[45] Date of Patent: May 7, 1996

[54] SOLUTION DISPENSER FOR AIR CONDITIONING MICROORGANISM CONTROL

[76] Inventor: Raymond D'Agaro, 1623 NE. 45th St., Fort Lauderdale, Fla. 33334

[21] Appl. No.: 290,614

[22] Filed: Aug. 15, 1994

[51] Int. Cl.$^6$ .............................. A61L 2/18; A61L 2/24; F28G 13/00
[52] U.S. Cl. .............................. 422/116; 422/292; 62/78; 62/303; 137/216; 137/561 A
[58] Field of Search .............................. 422/5, 292, 106, 422/116; 62/78, 303; 137/216, 216.1, 143, 561 A

[56] References Cited

U.S. PATENT DOCUMENTS

| | | | |
|---|---|---|---|
| 3,884,265 | 5/1975 | Fry et al. | 137/565 |
| 3,990,855 | 11/1976 | Cort et al. | 137/268 X |
| 4,545,956 | 10/1985 | Ciszewski et al. | 422/116 X |
| 4,702,679 | 10/1987 | Malbec | 417/475 |
| 5,145,641 | 9/1992 | Shelley | 422/26 |
| 5,195,334 | 3/1993 | Lang et al. | 62/305 |
| 5,289,691 | 3/1994 | Schlosser et al. | 62/78 |

FOREIGN PATENT DOCUMENTS 58-56909  4/1983  Japan ............................. 62/78

*Primary Examiner*—Robert J. Warden
*Assistant Examiner*—E. Leigh Dawson
*Attorney, Agent, or Firm*—Alvin S. Blum

[57] ABSTRACT

Microorganism growth within water chambers of air conditioning systems is controlled by the periodic introduction of minute quantities of biocidal materials. A large volume reservoir holds a concentrated solution of biocidal material. A pump, fed from the reservoir, pumps the solution through a tube to the water chamber. The pump is actuated for very short duration periods so that only a very small volume of the solution is dispensed. The time interval between periods is very long so that the biocide concentration in the water chamber is renewed as required. The duration of the pumping periods and the time interval between periods are adjustable by controls in a timer. A normally closed check valve in the line keeps the line full between periods. An antisiphon mechanism is provided in the line when it branches. An alarm mechanism is optionally provided to warn when the reservoir solution is depleted.

10 Claims, 1 Drawing Sheet

U.S. Patent
May 7, 1996
5,514,344
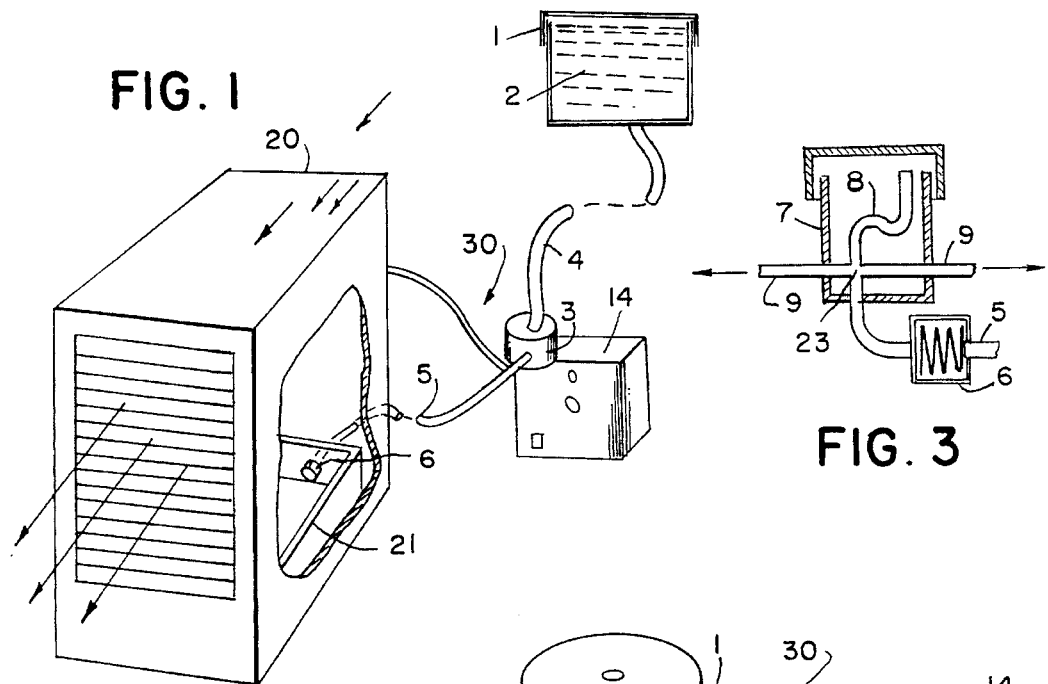
FIG. 1
FIG. 3
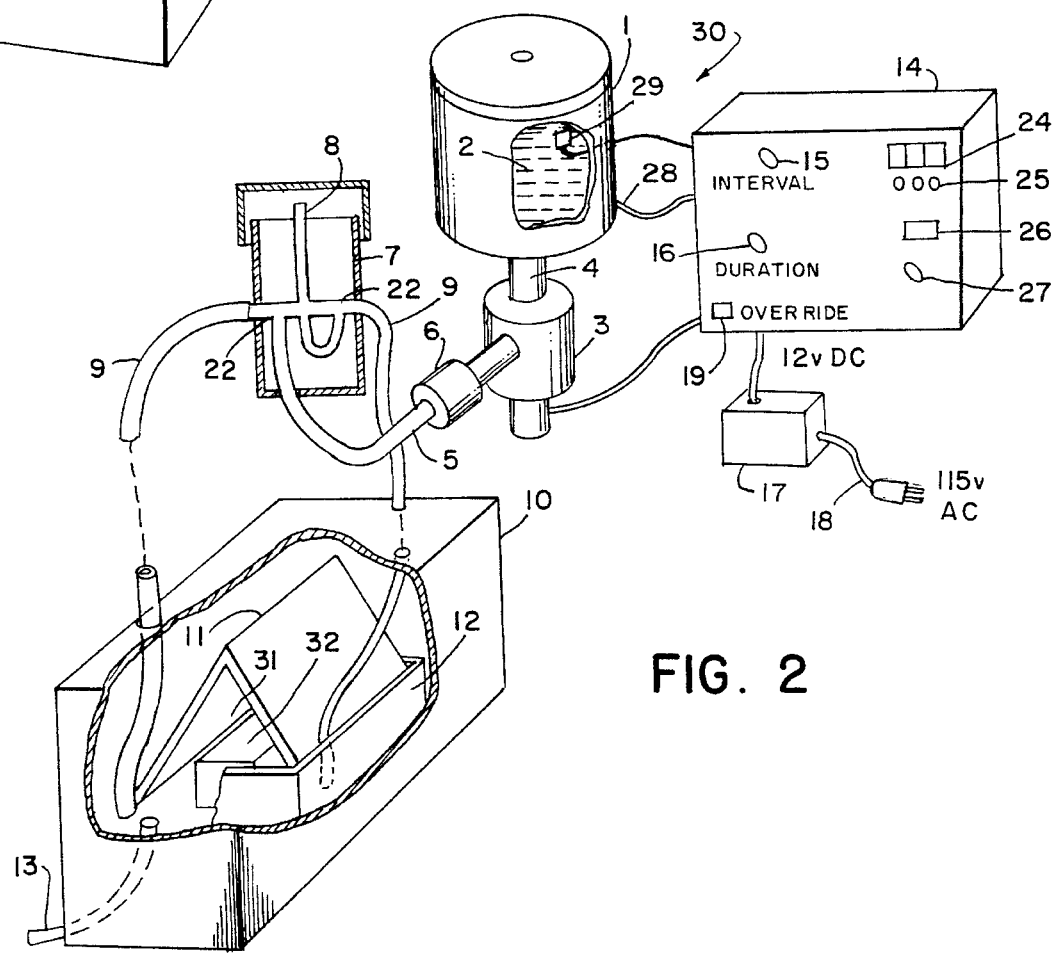
FIG. 2

SOLUTION DISPENSER FOR AIR CONDITIONING MICROORGANISM CONTROL

This invention relates to water chambers exposed to the atmosphere in air conditioning systems, and more particularly to devices for preventing the build up of algae, bacteria, mold and the like in condensate pans of air conditioning units by the periodic introduction of biocidal liquid therein.

BACKGROUND OF THE INVENTION

Condensate pans and plumbing in the air handling units of air conditioners are exposed to the atmosphere which contains many microorganisms. Some of these enter the water and multiply. The build up may mechanically obstruct outflow passages, causing overflow of condensate, for example. In an unattended apartment, in a multistory building, this causes considerable property damage and liability disputes. In certain situations, pathogenic microorganisms may grow in a cooling tower, resulting in a Legionaire's disease epidemic, for example.

Prior art solutions have included periodic cleaning and manual introduction of biocidal material into the condensate pan in liquid form, as solids such as large tablets or briquettes which slowly dissolve, and pads which slowly diffuse their biocidal contents into the water. These approaches are labor intensive, apply treatment in an inconsistent and nonuniform manner to either provide inadequate concentrations or wasteful amounts or both such as a high concentration that diminishes as the material is progressively eluted or dissolved.

SUMMARY OF THE INVENTION

It is accordingly an object of the invention to provide a completely automatic, controlled system for applying biocidal material to treat condensate pans of air handling units of air conditioners uniformly and consistently in which the necessary amounts may be dispensed efficiently with greatly reduced labor costs to ensure the prevention of build-up so that the equipment will operate consistently and safely for prolonged unattended periods. The dispenser system of the invention comprises: a reservoir holding a large volume of a highly concentrated solution having a biocidal action for preventing growth of microorganisms; an adjustable timer mechanism for applying electric power for predetermined brief time intervals spaced apart by predetermined long time intervals; power drive means actuated by the electric power for dispensing small fractions of the reservoir solution through a narrow tube to a remote location and into condensate pans of air conditioning units.

These and other objects, advantages and features of the invention will become more apparent when the detailed description is studied in conjunction with the drawings.

BRIEF DESCRIPTION OF THE DRAWINGS

FIG. 1 is a diagrammatic perspective view of a system of the invention.

FIG. 2 is a diagrammatic perspective view of another embodiment of the invention.

FIG. 3 is a diagrammatic sectional view of another antisiphon distributor of the invention.

DETAILED DESCRIPTION OF PREFERRED EMBODIMENTS

Referring now first to FIG. 1, a water cooling tower 20 such as may be seen on the roof of an air conditioned institutional building has within it well known features, not shown, for cooling hot water by spraying it into a stream of cooling air or passing it over a large surface area exposed to air, catching it within a sump chamber 21, and recirculating it. Evaporative coolers operate in a similar manner in arid environments with the air being used for building cooling after exposure to the water. As microorganisms from the air are deposited in the warm recirculated water, they feed on nutrients also deposited in the water. Over a period of time, the growth will foul the plumbing and heat exchange surfaces, greatly impairing efficiency. The pump dispensing system 30 of the invention suppresses the growth by periodically introducing small amounts of biocide into the sump chamber 21. The dispensing system may be positioned close to, or remote from the tower 20 as preferred, for convenience and access. Since it is often awkward to get onto the roof, it may be located on a lower floor, with only a very small tube 5 leading into the sump. A reservoir 1 contains a high concentration of a biocidal solution 2. The solution may contain biocides of the type well known in the art, including the quaternary ammonium compounds, for example. A tube 4 from the reservoir leads to a pump 3, whose output tube 5 contains a one way, normally closed, check valve so that water from the sump cannot siphon back into the dispenser apparatus, which may be at a lower level, and to keep line 5 full of the solution. The pump and reservoir may be spaced apart as required. Electric power to pump 3 is provided by timer 14. The timer may be adjusted to provide power to the pump for a duration of ½ to 1 second, for example, at spaced apart intervals of 1–12 times per day, for example.

FIG. 2 shows a typical air handler 10 with a pair of evaporator coils 11 sitting in a condensate pan of the type having a perimeter channel 31 with open center 32. As water condenses on the coils, it drains into the pan, and then drains from the pan through drain 13 to waste. Because this is the type of air handler commonly used in residences, overflowing of the condensate from a clogged drain can have very expensive consequences. In order to ensure that the biocide is effectively delivered to all areas of the pan 12, multiple points of entry of the solution into the pan may be required. Two tubes 9 deliver solution to the two sides of the pan. A distributor 7 ensures that the tubes 9 are sufficiently empty after the pump turns off, such that siphoning between the tubes 9 cannot occur. Vacuum breaking antisiphon tube 8 lets in enough air to break any siphoning action.

The pump 3 may be of the type used by automobile windshield washers with the reservoir resting on it, that is powered by 12 volts D.C. power. The timer 14 has an adjustable control 16 for duration of power application and control 15 for time interval between operations. These controls may be any of the mechanical or electronic controls of the type well known in the art. Because the volume of solution dispensed during each "ON" period may be minute, the override control 19 may be provided for continuous pumping to prime the lines. This control should be spring loaded so that it cannot be left on inadvertently. The power may come from line cord 18 through 12 volt D.C. transformer/rectifier 17.

While the distributor of FIG. 2 uses two T tubes 22, FIG. 3 shows an alternative embodiment of the distributor in which the antisiphon tube comes off the top of a cross connector 23. The check valve 6 should be in line 5 to the distributor 7.

The system is readily adaptable to a variety of field conditions using the same structure, and one system may feed multiple air handlers. The electrical components may be installed close to an electric power source, which may be remote from the water pan. It may be powered in tandem with power to the air conditioner so that solution is not dispensed when not required. The reservoir may be installed at a location most accessible for refilling. The timer may be set for various durations of operation and for various intervals between operations as dictated by the concentration of biocide solution employed and the requirements of a particular application.

For further assurance of efficacy of a system designed to go for prolonged periods without attention, a variety of mechanisms may be provided to warn the operator when the reservoir must be refilled. A float sensor 29 in the reservoir may actuate an audible or visible alarm 27 when the solution drops below a preset level. Alternatively, two contacts 28 in the solution may actuate the alarm 27 when the solution drops below them and the electrical conductivity between them changes. A purely electronic mechanism may also be employed, as also shown in FIG. 2, wherein an indicating totalizer 24 adds up and displays the total number of actuations since resetting to zero with reset 26. The pump is run at very short intervals for the required durations until the reservoir is empty and totalizer 24 displays the total number of actuations which will just empty the reservoir. The setting knobs 25 are set to this number, the interval reset to the desired time, and the totalizer 24 is reset to zero with control 26 every time the reservoir is refilled. When the totalizer reaches this preset number, the alarm 27 will be actuated to remind the operator to refill the reservoir.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A system for controlling the growth of microorganisms in the water of condensate pans of air conditioning units, the system comprising:

A) at least one condensate pan of an air conditioning unit which is unattended for periods of time, said condensate pan adapted for unobstructed drainage to waste;

B) a volume reservoir means for containing a concentrated biocidal solution;

C) only one pump having an inlet and an outlet for periodically forcing a fraction of said solution from said inlet through said outlet under pressure;

D) a first fluid connection between said inlet and said reservoir means at the bottom thereof for conducting said fraction of said solution from said reservoir means to said only one pump;

E) a second fluid connection between said outlet and said at least one condensate pan;

F) a normally closed, one-way check valve interposed in said second fluid connection for permitting fluid flow therein from said outlet to said at least one condensate pan only when under pressure, said valve preventing reverse fluid flow;

G) electric power means for operating said only one pump for preset intervals of time for periodically dispensing fractions of said solution from said reservoir means; and H) timer means operatively connected to said electric power means for adjustably controlling the duration of said preset intervals of time when said pump means is operating and the time between said intervals to enable said at least one pan to be periodically provided with said solution during an unattended period of time, to ensure unobstructed drainage to waste.

2. The system according to claim 1, further comprising antisiphon means in said second fluid connection between said check valve and said at least one condensate pan, and at least two fluid channels connecting said antisiphon means with said at least one condensate pan, said antisiphon means preventing siphoning of fluid between said at least two fluid channels.

3. The system according to claim 1, further comprising alarm means for providing human sensible warning that said solution in said reservoir means requires refilling.

4. The system according to claim 3, in which said alarm means includes a float mechanism in said reservoir.

5. The system according to claim 3, in which said alarm means includes means for counting number of operations of said pump.

6. The system according to claim 3, in which said alarm means includes conductivity sensing means in said reservoir means for sensing presence or absence of said solution.

7. The system according to claim 1, in which said reservoir means is mounted on top of said pump means.

8. The system according to claim 1, further comprising timer override control means for providing manually controlled continuous pump operation.

9. The system according to claim 1, in which said pump means is an automobile windshield washer fluid dispensing pump.

10. A system for controlling the growth of microorganisms in the water condensate pans of air conditioning units, the system comprising:

A) a volume reservoir means for containing a concentrated biocidal solution;

B) a pump means having an inlet and an outlet for forcing a solution from said inlet through said outlet under pressure;

C) a first fluid connection between said inlet and said reservoir means at the bottom thereof for conducting a solution from said reservoir means to said pump means;

D) a second fluid connection between said outlet and at least one water condensate pan of an air conditioning unit which is unattended for periods of time;

E) a normally closed, one-way check valve interposed in said second fluid connection for permitting fluid flow therein from said outlet to said at least one condensate pan only when under pressure, said valve preventing reverse fluid flow;

F) electric power means for operating said pump means for preset intervals of time for dispensing fractions of a solution from said reservoir means;

G) timer means operatively connected to said electric power means for adjustably controlling the duration of said preset intervals of time when said pump means is operating and the time between said intervals to enable said at least one pan to be periodically provided with a solution during an unattended period of time; and H) antisiphon means in said second fluid connection between said check valve and said at least one condensate pan, and at least two fluid channels directly connecting said antisiphon means with said at least one condensate pan, said antisiphon means preventing siphoning of fluid between said at least two fluid channels.

* * * * *